(12) United States Patent
Imai et al.

(10) Patent No.: US 7,390,490 B1
(45) Date of Patent: Jun. 24, 2008

(54) USES OF ANTI-CX3CR1 ANTIBODY, ANTI-FRACTALKINE ANTIBODY AND FRACTALKINE

(75) Inventors: Toshio Imai, Kyoto (JP); Miyuki Nishimura, Kyoto (JP); Kenzo Muramoto, Tsukuba (JP); Yoshikazu Kuboi, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 21 days.

(21) Appl. No.: 11/225,829

(22) Filed: Sep. 13, 2005

Related U.S. Application Data

(62) Division of application No. 09/963,316, filed on Sep. 25, 2001.

(30) Foreign Application Priority Data

Mar. 19, 2001 (JP) .............................. 2001-077384

(51) Int. Cl.
*A61K 39/395* (2006.01)
*C07K 16/24* (2006.01)
*C07K 16/28* (2006.01)

(52) U.S. Cl. ............... 424/144.1; 424/152.1; 424/172.1; 424/184.1; 424/810; 530/388.22; 530/388.23; 530/388.25; 530/389.2; 530/389.3; 530/389.6

(58) Field of Classification Search ............... 424/144.1, 424/152.1, 172.1, 184.1, 810; 530/388.22, 530/388.23, 388.25, 389.2, 389.3, 389.6
See application file for complete search history.

(56) References Cited

U.S. PATENT DOCUMENTS 6,013,257 A 1/2000 Pan

FOREIGN PATENT DOCUMENTS

JP 2001-218581 8/2001

OTHER PUBLICATIONS

Dorland's Illustrated Medical Dictionary, 27th Edition [1988]. Taylor et al, eds., W.B Saunder Co, Philadelphia, PA, pp. 1089 and 1460.*
Ruth et al. Arthritis & Rheumatism [Jul. 2001] 44(7):1568-1581.*
Wong et al. Cardiovascular Pathology [2002] 11:332-338.*
T. Imai et al., "Identification and Molecular Characterization of Fractalkine Receptor CX3CR1, which Mediates Both Leucokyte Migration and Adhesion", *Cell*, 91: 521-530, Nov. 14, 1997.
L. Feng et al., "Prevention of crescentic glomerulonephritis by immunoneutralization of the fractalkine receptor CX3CR1. Rapid Communication", *Kidney International*, 56: 612-620, 1999.
*Proceedings of the Japanese Society for Immunology*, 30: p. 192, 2-F-270-P/O, 2000.
D.M. Hoover et al., "The Crystal Structure of the Chemokine Domain of Fractalkine Shows a Novel Quaternary Arrangement", *J. Biol. Chem.*, 275: 23187-23193, 2000.
A.D. Lucas et al., "The Transmembrane Form of the CXCL1 Chemokine Fractalkine is Expressed Predominantly by Epithelial Cells in Vivo", *Am. J. Pathol.*, 158: 855-866, 2001.
A. Campbell et al., "General Properties and Applications on Monoclonal Antibodies" in Monoclonal Antibody Technology, 1985, pp. 1-32.
J.K. Harrison et al., "Role for neuronally derived fractalkine in mediating interactions between neurons and CX3CR1-expressing microglia", Proc. Natl. Acad. Sci. USA, 1998, 95: 10896-10901.
Notice of Reason for Rejection mailed on Dec. 12, 2006 in corresponding Japanese application No. 2001-308619 (and corresponding English Translation).
O. Yoneda et al., "Effects of Fractalkine on NK cell activity and NK cell-mediated damage of endothelial cells", *J. Osaka Odontol. Soc.*, 1999, 62(2): 90-97 (and English translation of abstract).
O. Yoneda et al., "Fractalkine-mediated endothelial cell injury by NK cells", *J. Immunol.*, 2000, 164: 4055-4062.
Verified Translation of Japanese patent application No. JP 2001-077384.

* cited by examiner

*Primary Examiner*—Christina Chan
*Assistant Examiner*—F. Pierre VanderVegt
(74) *Attorney, Agent, or Firm*—Brenda Herschbach Jarrell; Choate, Hall & Stewart, LLP

(57) ABSTRACT

There are provided uses of an antibody directed to CX3CR1 and fractalkine. Killer lymphocytes can be readily identified, eliminated and separated by using an anti-CX3CR1 antibody. Further, there can be provided an antibody drug for suppressing chemotaxis and cytotoxic activity of killer lymphocytes by suppressing an interaction between CX3CR1 and fractalkine.

7 Claims, 10 Drawing Sheets

USES OF ANTI-CX3CR1 ANTIBODY, ANTI-FRACTALKINE ANTIBODY AND FRACTALKINE

RELATED APPLICATIONS

The present application is a divisional application claiming the benefit of priority under 35 U.S.C. § 120 of co-pending U.S. patent application Ser. No. 09/963,316 filed Sep. 25, 2001, which is incorporated herein by reference in its entirety. The application further claims priority under 35 U.S.C. § 119 of JP 2001-77384 filed Mar. 19, 2001, which is also incorporated herein by reference in its entirety.

BACKGROUND OF THE INVENTION

The present invention relates to applications of an antibody directed to CX3CR1, an antibody directed to fractalkine and fractalkine.

Killer lymphocytes play a central role in elimination of pathogens that invade into living bodies, abnormal cancer cells and so forth. However, their excessive cytotoxic reactions sometimes destroy normal tissues and they are tightly associated with onsets of autoimmune diseases such as nephritis, rheumatism, diabetes mellitus and myocarditis. Killer lymphocytes are classified into NK cells, CD8T cells, CD4T cells, γδ T cells, NKT cells and so forth, which commonly have a mechanism for inducing apoptosis of a target cell. The most known mechanism is mediated by perforin, which is a pore-forming protein, and granzyme B, which is a serine protease, released from cytotoxic secretory granules of the killer lymphocytes. Perforin forms pores in target cells, and then granzyme B is mobilized from these pores into the target cells and induces apoptosis of the target cells. Further, FasL and TARIL belonging to the TNF family are expressed or secreted on the cell surface of killer lymphocytes, bound to a receptor on the target cells and induce apoptosis. The cytotoxic mechanism and the activation mechanism of killer lymphocytes have been studied in detail, but little is known about factors for regulating migration of these cells in living bodies.

Infiltration of lymphocytes from the bloodstream into an inflammatory tissue is considered to require multistep reactions involving cell adhesion molecules and cellular chemotactic factors. In a typical infiltration mechanism, an initial reaction is contact and rolling of lymphocytes on endothelial cells. These are mainly performed by adhesion molecules called selectin. By performing the rolling, the lymphocytes become able to sense cellular chemotactic factors locally produced and presented on vascular endothelial cells. The cellular chemotactic factors activate adhesion molecules called integrin mainly by signal transduction via a G protein-coupled seven-transmembrane receptor and induce strong adhesion between lymphocytes and endothelial cells. Then, finally, lymphocytes are infiltrated into a tissue through intercellular spaces of endothelial cells.

Chemokines are major cellular chemotactic factors in living bodies and regulate tissue infiltration of lymphocytes through acceleration of cell motility and activation of cell adhesion molecules. Chemokines are classified into four subfamilies, CC, CXC, C and CXXXC, depending on the sequence of their first two cysteine residues. Members of the CC, CXC and C chemokine subfamilies are secretory proteins composed of about 70 amino acids. Although they themselves do not have activity as adhesion molecules, they can induce cell adhesion. Secreted chemokines are bound to seven-transmembrane receptors on the surface of target cells and activate integrin through a trimer G protein to induce cell adhesion and migration. The cell-type specific activity of a chemokine is primarily determined by whether its specific receptor exists in a certain cell subset. Therefore, cell-type specificity of a chemokine bound to the receptor can be revealed by closely investigating an expression state of a specific chemokine receptor on lymphocytes for each cell subset.

Recently, in addition to the previously revealed cellular chemotactic mechanism, a novel simple lymphocyte infiltration mechanism was identified. This mechanism is mediated by fractalkine, which is expressed on activated endothelial cells, and a seven-transmembrane receptor, CX3CR1, which is expressed on monocytes, NK cells and a part of T cells in the bloodstream. Fractalkine is the only member of the CXXXC chemokine subfamily and has distinct structural and functional characteristics, which cannot be observed in other chemokines. Fractalkine is expressed on the cell surface as a membrane-bound chemokine which has a chemokine domain, a mucin domain, a transmembrane domain and an intracytoplasmic domain. When the membrane-bound fractalkine binds to CX3CR1, it can solely mediate strong adhesion without mediation by selectins or integrins even at a physiological blood flow rate. That is, the fractalkine-CX3CR1 cellular infiltration system mediates, by one-step reaction, the same function as that of the multistep cellular infiltration mechanism mediated by selectins and integrins. Further, secretory fractalkine secreted by shedding from the membrane-bound fractalkine binds to CX3CR1 and induces activation of integrin and cell chemotaxis as in the case of the known chemokines.

Further, expression of fractalkine is induced by treating vascular endothelial cells with inflammatory cytokines such as TNF or IL-1. CX3CR1 is expressed on monocytes, most of NK cells and a part of T cells, but not on neutrophils. Therefore, the fractalkine CX3CR1-cellular infiltration system is considered to be an extremely efficient mechanism for recruiting a kind of immunocytes onto endothelial cells of a damaged tissue or into the tissue. However, kinds of cells migrated by the cellular infiltration system and actions of the cellular infiltration system in inflammatory reactions have not been analyzed.

SUMMARY OF THE INVENTION

The inventors of the present invention identified cells migrated by the fractalkine-CX3CR1 cellular infiltration system and elucidated importance of the cellular infiltration system in the inflammatory reactions.

That is, as a result of analyzing characteristics of CX3CR1-expressing lymphocytes by using an antibody directed to CX3CR1 in detail, they revealed that CX3CR1 was selectively expressed on killer lymphocytes containing perforin and granzyme B in the cells. Further, in CD8-positive T cells, cytotoxic activity was selectively observed in CX3CR1-positive cell fractions.

Further, they revealed that secretory fractalkine selectively induced cell chemotaxis of killer lymphocytes containing perforin and granzyme B and that this cell chemotaxis was inhibited by an anti-fractalkine antibody. Further, they also revealed that membrane-bound fractalkine enhanced killer lymphocyte chemotaxis induced by another chemokine, MIP-1β, and that this enhancement was suppressed by an anti-fractalkine antibody.

From the above results, is was demonstrated that the fractalkine-CX3CR1 cellular infiltration system was composed of extremely important chemokine and adhesion molecules for leading killer lymphocytes to a target tissue. It is considered that elimination of killer lymphocytes from tissues suffering from autoimmunization, recruitment of killer lymphocytes to cancer tissues and so forth can be achieved by regulating this system. The present invention was accomplished based on these findings.

That is, the present invention provides the following.

(1) A method for separating or eliminating killer lymphocytes, which comprises allowing an antibody directed to CX3CR1 to bind to lymphocytes and separating the lymphocytes by FACS or MACS using the binding of the antibody as an index.

(2) A reagent for separating or eliminating killer lymphocytes used for the method as defined in (1), which comprises an antibody directed to CX3CR1 and a carrier.

(3) A method for identifying killer lymphocytes, which comprises labeling lymphocytes with an antibody directed to CX3CR1 and identifying the killer lymphocytes by FACS based on the label.

(4) A reagent for identifying killer lymphocytes used for the method as defined in (3), which comprises an antibody directed to CX3CR1 and a carrier.

(5) A method for identifying killer lymphocytes, which comprises immunohistostaining lymphocytes by using an antibody directed to CX3CR1.

(6) A reagent for identifying killer lymphocytes used for the method as defined in (5), which comprises an antibody directed to CX3CR1 and a carrier.

(7) A therapeutic agent for an autoimmune disease, which comprises an antibody that binds to CX3CR1 or fractalkine and inhibits chemotaxis of killer lymphocytes by suppressing an interaction between CX3CR1 and fractalkine, and a pharmaceutically acceptable carrier.

(8) The therapeutic agent for an autoimmune disease according to (7), wherein the antibody binds to fractalkine.

(9) A method for treating an autoimmune disease, which comprises administering a therapeutically effective amount of an antibody that binds to CX3CR1 or fractalkine and inhibits chemotaxis of killer lymphocytes by suppressing an interaction between CX3CR1 and fractalkine.

(10) The method for treating an autoimmune disease according to (9), wherein the antibody binds to fractalkine.

(11) A method for treating an autoimmune disease, which comprises inhibiting chemotaxis of killer lymphocytes by suppressing an interaction between CX3CR1 and fractalkine.

(12) An immunotoxin comprising an antibody directed to CX3CR1 and a cytotoxic substance bound to the antibody.

(13) A method for treating cancer, which comprises introducing a gene coding for fractalkine into a cancer cell so that fractalkine is expressed in an amount causing migration of killer lymphocytes.

(14) An agent for gene therapy of cancer, which comprises a gene coding for fractalkine and a pharmaceutically acceptable carrier.

CX3CR1 and fractalkine referred to herein are a chemokine receptor and a chemokine, respectively. Killer lymphocytes are lymphocytes having cytotoxic activity.

DETAILED DESCRIPTION OF THE INVENTION

Figure 1:
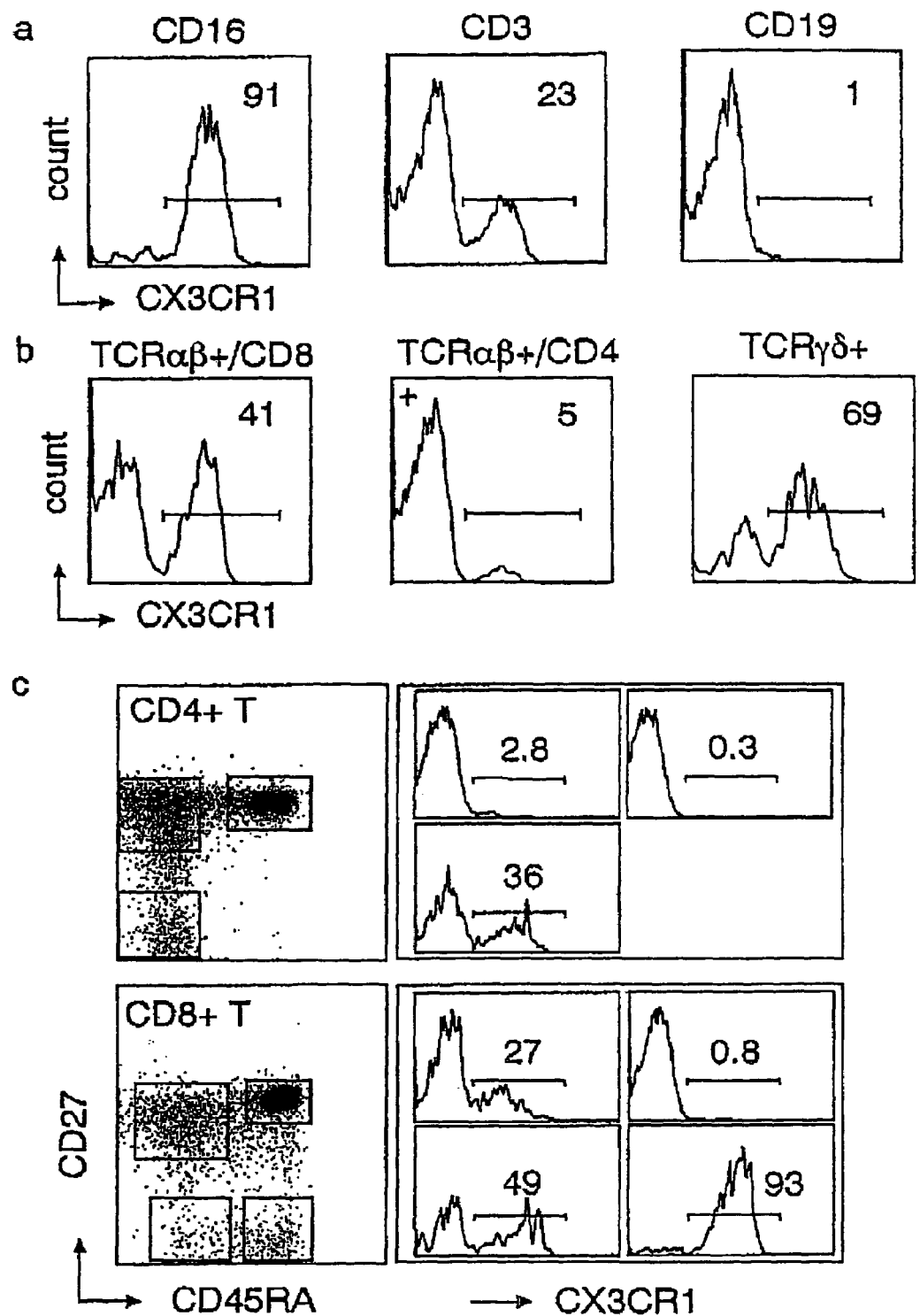
FIG. 1 shows lymphocyte subsets expressing CX3CR1.

<1> Uses of Antibody Directed to CX3CR1 or Fractalkine

An antibody directed to CX3CR1 or fractalkine can be produced as follows.

A mammal (for example, mouse, hamster or rabbit) can be immunized with CX3CR1, fractalkine or a protein fragment (for example, a peptide fragment) thereof in the form of an immunogen inducing an immune response in the mammal.

An expression vector incorporating a CX3CR1 or fractalkine gene (for example, GenBank NM 001337 or NM 002996) can be expressed in host cells such as, for example, bacteria, mammal cell lines or insect cell lines, and CX3CR1 or fractalkine can be purified from a culture booth, microbial cells or cells according to a standard method. Further, CX3CR1 or fractalkine may be expressed as a fusion protein with, for example, GST or the like, and may be purified by using a glutathione column in the case of a fusion protein with GST. The peptide of CX3CR1 or fractalkine can be synthesized based on the amino acid sequence of CX3CR1 or fractalkine by a known method (for example, F-moc or T-boc chemical synthesis), and immunogenicity of the synthesized peptide may be increased by binding it to an appropriate carrier, for example, KLH.

After immunization with purified CX3CR1, fractalkine or a peptide fragment thereof together with an adjuvant, antiserum can be obtained, and a polyclonal antibody can be isolated from the antiserum if desired. Further, to produce a monoclonal antibody, antibody-producing cells (lymphocytes) are recovered from an immunized animal and fused with myeloma cells by a standard cell fusion method to immortalize the cells and thus obtain hybridoma cells. Such a technique is an established method in this field and can be performed according to description of an appropriate manual (Harlow et al, Antibodies: A Laboratory Manual, Cold Spring Harbor Laboratory, 1998). Further, a monoclonal antibody may also be produced by other methods for producing a human monoclonal antibody such as the human B cell hybridoma method (Kozbar et al., Immunol. today, 4: 72, 1983), the EBV-hybridoma method (Cole et al., Monoclonal Antibody in Cancer Therapy, Allen R. Bliss, Inc., pp. 77-96, 1985) and screening of a combinatorial antibody library (Huse et al., Science, 246: 1275, 1989).

As another method, there can be used a method wherein a mammal is immunized with insect cells expressing CX3CR1 as they are, a hybridoma is produced from the lymphocytes of the mammal and the produced antibodies are screened by using mammalian cells expressing CX3CR1 (having low cross immunity with the insect cell and not bound to an antibody directed to a protein derived from the insect cell).

The present inventors found that CX3CR1 was specifically found in lymphocytes containing perforin and granzyme B and having cytotoxic activity, and when the lymphocytes were fractionated into CX3CR1-positive cells and CX3CR1-negative cells, the cytotoxic activity was observed only in the CX3CR1-positive cells, and thus CX3CR1 could be used as a novel marker of killer lymphocytes. That is, since CX3CR1 is expressed specifically in the killer lymphocytes, and antibody directed to CX3CR1 (anti-CX3CR1 antibody) can be used for the following purposes:

separation or elimination of killer lymphocytes by allowing an antibody directed to CX3CR1 to bind to the killer lymphocytes in separation of the lymphocytes by FACS or MACS;

identification of killer lymphocytes by labeling the killer lymphocytes with an antibody directed to CX3CR1 in an analysis of lymphocytes by using FACS; and identification of killer lymphocytes by staining the killer lymphocytes with an antibody directed to CX3CR1 in a histochemical staining using an antibody.

The anti-CX3CR1 antibody can be used as a reagent used for the above purposes by combining it with a carrier (water, a buffer or the like) suitable for the above purposes.

Therefore, the present invention provides the following.

A method for separating or eliminating killer lymphocytes, which comprises allowing an antibody directed to CX3CR1 to bind to lymphocytes and separating the lymphocytes by FACS or MACS using the binding of the antibody as an index, and a reagent for separating or eliminating killer lymphocytes used for the method, which comprises an antibody directed to CX3CR1 and a carrier.

A method for identifying killer lymphocytes, which comprises labeling lymphocytes with an antibody directed to CX3CR1 and identifying the killer lymphocytes by FACS based on the label, and a reagent for identifying killer lymphocytes used for the method, which comprises an antibody directed to CX3CR1 and a carrier.

A method for identifying killer lymphocytes, which comprises immunohistostaining lymphocytes by using an antibody directed to CX3CR1, and a reagent for identifying killer lymphocytes used for the method, which comprises an antibody directed to CX3CR1 and a carrier.

Specifically, if a tissue section wherein infiltration of lymphocytes is observed is stained by a fluorescent antibody method or an enzyme antibody method by using an anti-CX3CR1 antibody, whether the infiltration lymphocytes are lymphocytes having killer activity or not can be determined.

Further, if FACS analysis is performed by using an anti-CX3CR1 antibody, the proportion of lymphocytes having killer activity included in the cell population can be readily measured.

The anti-CX3CR1 antibody is further effective to fractionate killer lymphocytes by FACS or MACS. Since CX3CR1 exists on the cell surface and the anti-CX3CR1 antibody binds even to intact cells, the killer lymphocytes can be fractionated with their activity maintained.

Since CX3CR1 exists on the cell surface and the anti-CX3CR1 antibody binds even to an intact cell, if peripheral blood is perfused to a column obtained by immobilizing an anti-CX3CR1 antibody on an appropriate support as a solid phase or the like, killer lymphocytes can be eliminated ex vivo. Further, if an immunotoxin is prepared by binding a CX3CR1 antibody or secretory fractalkine to a toxin, or after the binding of the anti-CX3CR1 antibody, a complement is allowed to bind to it so that it is activated, killer lymphocytes can be eliminated in vivo.

The antibody binding to CX3CR1 or fractalkine does not necessarily inhibit an interaction between CX3CR1 and fractalkine. In fact, the monoclonal antibodies directed to CX3CR1 obtained by the inventors of the present invention, 2A9-1 and 1F2-2, did not inhibit the interaction.

The inventors of the present invention further selected an antibody that inhibited an interaction between CX3CR1 and fractalkine from antibodies that bound to CX3CR1 or fractalkine, and found that, if such an antibody was used, infiltration of killer lymphocytes responsible for cytotoxic activity in an autoimmune disease or the like could be effectively suppressed. Therefore, the present invention provides uses of such an antibody. That is, the present invention provides a therapeutic agent for an autoimmune disease comprising an antibody that binds to CX3CR1 or fractalkine and inhibits chemotaxis of killer lymphocytes by suppressing an interaction between CX3CR1 and fractalkine, and a pharmaceutically acceptable carrier, and a method for treating an autoimmune disease, which comprises administering a therapeutically effective amount of an antibody that binds to CX3CR1 or fractalkine and inhibits chemotaxis of killer lymphocytes by suppressing an interaction between CX3CR1 and fractalkine.

In the therapeutic agent and the treatment method, the antibody is preferably one that binds to fractalkine The antibody inhibiting an interaction between CX3CR1 and fractalkine can be screened by determining whether a CX3CR1-positive cell migrates to a cell expressing fractalkine or membrane-bound fractalkine or not. A specific screening method by determining whether the CX3CR1-positive cell migrates or not will be described below, but the present invention is not limited to this method.

Chemotaxis in response to fractalkine can be determined by using, for example, a trans-well culture insert (Coaster).

Cells not expressing fractalkine, for example, ECV304 cells, are cultured on a trans-well culture insert to form a monolayer of the cells on the upper surface of the culture insert. Fractalkine is diluted with a chemotaxis solution (for example, RPMI-1640:M199=1:1, 0.5% BSA, 20 mM HEPES, pH 7.4) to an appropriate concentration, preferably a concentration of 10 nM, and added to a 24-well plate. The trans-well culture insert, on which ECV304 cells are cultured, is mounted on a 24-well trans-well, and an appropriate number, preferably $10^6$, of peripheral blood mononuclear cells suspended in the chemotaxis solution are added to the trans-well culture insert. After the cells are cultured under appropriate conditions, preferably at 37° C. for 4 hours, cells that transmigrate to the well plate through the ECV304 cells are recovered and identified based on a cell surface marker or intracellular antigen. Preferably, the cells are fluorescence-stained using fluorescence-labeled cell surface marker or antibody directed to an intracellular antigen and then quantified by using a FACS calibur.

To the chemotaxis solution, an antibody that binds to CX3CR1 or fractalkine is added, and if chemotaxis of killer lymphocytes, preferably a cell expressing perforin and granzyme B or CX3CR1, more preferably a cell expressing CX3CR1, is suppressed, it is determined that the antibody inhibits an interaction between CX3CR1 and fractalkine.

Further, it can also be determined whether the antibody inhibits an interaction between CX3CR1 and fractalkine or not by allowing the ECV304 cells to express membrane-bound fractalkine and measuring peripheral blood mononuclear cells that migrate to other chemokines such as MIP-1β.

When the treatment method and therapeutic agent of the present invention are applied to humans, the following embodiments are preferred.

When a monoclonal antibody prepared by using an animal other than human, for example, a mouse monoclonal antibody prepared by using a mouse as an immune animal is administered to a human, it is recognized as a foreign protein and an immune response to the monoclonal antibody often occurs. A method for avoiding this problem is use of a chimera antibody, that is, an antibody wherein the antigen-binding region is derived from the mouse monoclonal antibody and other regions are derived from a human antibody. The antibody used in the present invention also includes a chimera antibody. Examples of the chimera antibody include a chimera antibody using the whole variable region of a mouse monoclonal antibody as an antigen-binding region (Morrison et al., Proc. Natl. Acad. Sci. USA, 81: 6851, 1985; Takeda et al., Nature, 314: 452, 1985) and a chimera antibody using a combination of a human-derived framework region and a hypervariable region derived from a mouse monoclonal antibody as an antigen-binding region (Teng et al., Proc. Natl. Acad. Sci. USA, 80: 7308-12, 1983; Kozbar et al., Immunol. Today, 4: 7279, 1983), but the present invention is not limited to these.

The antibodies referred to in the present specification also include an antibody fragment that specifically binds to CX3CR1 or fractalkine, for example, a Fab or (Fab')$_2$ fragment.

The therapeutic agent of the present invention can be administered to a patient with a disease wherein excessive cytotoxic reactions caused by killer lymphocytes occur, for example, autoimmune diseases such as nephritis, rheumatism, diabetes mellitus and myocarditis.

The therapeutic agent of the present invention can be administered by an ordinary method such as injection (subcutaneous, intravenous injection or the like).

The form of the therapeutic agent is appropriately selected depending on the administration method. Examples of pharmaceutical compositions suitable for use as injection include a sterile aqueous solution (in the case of a water-soluble composition) or dispersion and a sterile powder for instantly preparing a sterile injection solution or dispersion. Any pharmaceutical composition suitable for use as injection must be sterilized, and it must have such fluidity that operation using a syringe should be easily performed. The composition must be stable under manufacturing and storage conditions and be protected from actions of contaminated microorganisms such as bacteria and fungi. The carrier may be, for example, water, ethanol, polyol (for example, glycerol, propylene glycol, polyethylene glycol and so forth) or a solvent or dispersion medium composed of an appropriate mixture thereof. Appropriate fluidity can be maintained by using a coating such as, for example, that of lecithin, or maintaining a required particle size in the case of dispersion, or using a surface active agent. Protection from actions of microorganisms is achieved by various antibacterial agents and antifungal agents, for example, paraben, chlorobutanol, phenol, ascorbic acid, thimerosal and so forth. In many cases, it is preferable that the composition contains an isotonic agent, for example, saccharides, polyalcohols such as mannitol and sorbitol, sodium chloride or the like. Sustained absorption of the composition for injection can be attained by mixing the composition with an agent for delaying absorption such as aluminum monostearate and gelatin.

The injection solution can be prepared by mixing an appropriate solvent with a required amount of an antibody directed to CX3CR1 or fractalkine together with one or a combination of the aforementioned ingredients if required and subjecting the mixture to sterilized filtration. The dispersion is generally prepared by mixing a sterile medium comprising a base dispersion medium and other required ingredients selected from the above with an active compound. In the case of sterile powder for preparing a sterile injection solution, preferred preparation methods are vacuum dehydration and lyophilization, by which powder of active ingredient and desired additional ingredients subjected to sterilized filtration beforehand can be obtained.

Dose of the therapeutic agent is an amount sufficient for preventing excessive cytotoxic reactions of killer lymphocytes and may vary depending on age, sex and susceptibility to drugs of patient, administration method, history of disease and so forth.

As described above, its is considered that killer lymphocytes can be, for example, eliminated from tissues suffering from autoimmunization or recruited to cancer tissues by regulating the fractalkine-CX3CR1 cellular infiltration system. Therefore, so long as an interaction between CX3CR1 and fractalkine can be inhibited, means other than an antibody binding to CX3CR1 or fractalkine can be used to treat an autoimmune disease. Therefore, the present invention provides a method for treating an autoimmune disease, which comprises inhibiting chemotaxis of killer lymphocytes by suppressing an interaction between CX3CR1 and fractalkine.

Further, the present invention provides an immunotoxin comprising an antibody directed to CX3CR1 and a cytotoxic substance bound to the antibody.

Examples of the toxic substance include saporin, ricin, *Pseudomonas* exotoxin, diphtheria toxin, chemotherapeutic agents and so forth. The antibody and the toxic substance can be bound by a conventional method used for preparation of an immunotoxin. The immunotoxin of the present invention shows proliferative suppression specific to CX3CR1-expressing cells.

<2> Uses of Fractalkine

Since fractalkine solely induces chemotaxis of killer lymphocytes, killer lymphocytes can be efficiently migrated to target cells by introducing the fractalkine gene into target cells by introducing the fractalkine gene into target cells of the killer lymphocytes, preferably cancer cells, by using, for example, a virus vector or the like. As a result, the target cells can be damaged.

Therefore, the present invention provides a method for treating cancer, which comprises introducing a gene coding for fractalkine into cancer cells so that fractalkine is expressed in an amount sufficient for causing migration of killer lymphocytes, and an agent for gene therapy of cancer, which comprises a gene coding for fractalkine and a pharmaceutically acceptable carrier.

The gene coding for fractalkine can be obtained by a known method such as PCR based on the known nucleotide sequence registered at GenBank NM 002996 or the like. The gene can be introduced according to a method used for conventional gene therapy except for using the gene coding for fractalkine as the gene.

EXAMPLES

The present invention will be further explained with reference to the following specific examples. However, the scope of the present invention is not limited to these examples.

Example 1

Identification of CX3CR1-Expression Cells

To identify CX3CR1-expressing lymphocyte subsets in peripheral blood, an anti-human CX3CR1 antibody was prepared. A WKY/Ncrj rat was immunized with human CX3CR1-expressing cells (cells prepared in Example 9 described later) to obtain monoclonal antibodies. When two kinds of typical monoclonal antibodies, 2A9-1 and 1F2-2, were examined, either of them reacted with the CX3CR1-expressing cells, but did not react with other chemokine receptor-expressing cells (CCR1, CCR2, CCR3, CCR4, CCR5, CCR6, CCR7, CCR8, and XCR1).

Peripheral blood was collected from a vein of a healthy subject according to EDTA blood collection, and mixed with an ACK solution (8.26 g of $NH_4Cl$, 1.0 g of $KHCO_3$, 0.037 g/1 L of EDTA-4Na) for 5 minutes to dissolve erythrocytes. The solution was centrifuged at 1,200 rpm at room temperature for 5 minutes to precipitate leukocytes, and the leukocytes were then suspended in a FACS solution (PBS containing 1% fetal bone serum, 2% human AB blood type serum and 0.02% $NaN_3$). To this leukocyte suspension, an anti-human CX3CR1 monoclonal antibody was added, and the mixture was allowed to react on ice for 30 minutes. The leukocytes were washed twice with the FACS solution, and a FITC-conjugated anti-rat IgG (H+L) antibody (Cedarlane) was added thereto. Then the mixture was allowed to react on ice for 30 minutes. The leukocytes were washed twice with the FACS solution, and the FACS solution containing 1% rat serum was added. Then the mixture was allowed to react on ice for 30 minutes so as to block unreacted FITC-conjugated anti-rat IgG (H+L) antibodies. Then, a combination of directly labeled antibodies against various cell surface markers was added to the mixture and allowed to react on ice for 30 minutes. The leukocytes were washed twice with the FACS solution and measured by using a FACS calibur (Becton-Dickinson).

1) Expression of CX3CR1 on Lymphocytes

It was found that CX3CR1 was expressed in almost all monocytes and a part of lymphocytes, but rarely expressed in granulocytes. Further, as a result of multiple staining of the lymphocyte subsets with cell surface markers, it was revealed that CX3CR1 was expressed in almost all CD16$^+$ NK cells and a part of CD3$^+$ T cells, but not in CD19$^+$ B cells (FIG. 1, a). Since similar results were obtained with 2 kinds of the monoclonal antibodies, 1A9-1 and 1F2-2, 2A9-1 was used for the following analysis.

2) Expression of CX3CR1 on T Cells

When the CD3$^+$ T cells were examined in more detail, expression of CX3CR1 was observed in a part of T cell receptor $\alpha\beta^+$ CD8$^+$ T cells and T cell receptor (TRC) $\gamma\delta^+$ T cells and only a small part of T cell receptor $\alpha\beta^+$ CD4$^+$ T cells (FIG. 1, b).

Further, CD4$^+$ T cells and CD8$^+$ T cells were classified into so-called naïve T cells and memory/effector T cells by using CD27 and CD45RA$^-$ as markers, and expression of CX3CR1 was analyzed.

Among CD4$^+$ T cells, expression of CX3CR1 was observed in a part of CD45RA$^-$ CD27$^-$ memory/effector T cells and only a small part of CD45RA$^-$ CD27$^+$ memory/effector T cells, but not observed in CD45RA$^+$ CD27$^+$ naïve T cells.

Among CD8$^+$ T cells, expression of CX3CR1 was observed in a majority of CD45RA$^+$ CD27$^-$ effector. T cells and a part of CD45RA$^-$ CD27$^-$ and CD45RA$^+$ CD27$^+$ memory/effector T cells, but not observed in CD45RA$^+$ CD27$^+$ naïve T cells (FIG. 1, c).

Example 2

Correlation Between CX3CR1-Expressing Cells and Killer Lymphocytes

1) Correlation Between Expression of CX3CR1 and Killer Cell Surface Markers

Figure 2:
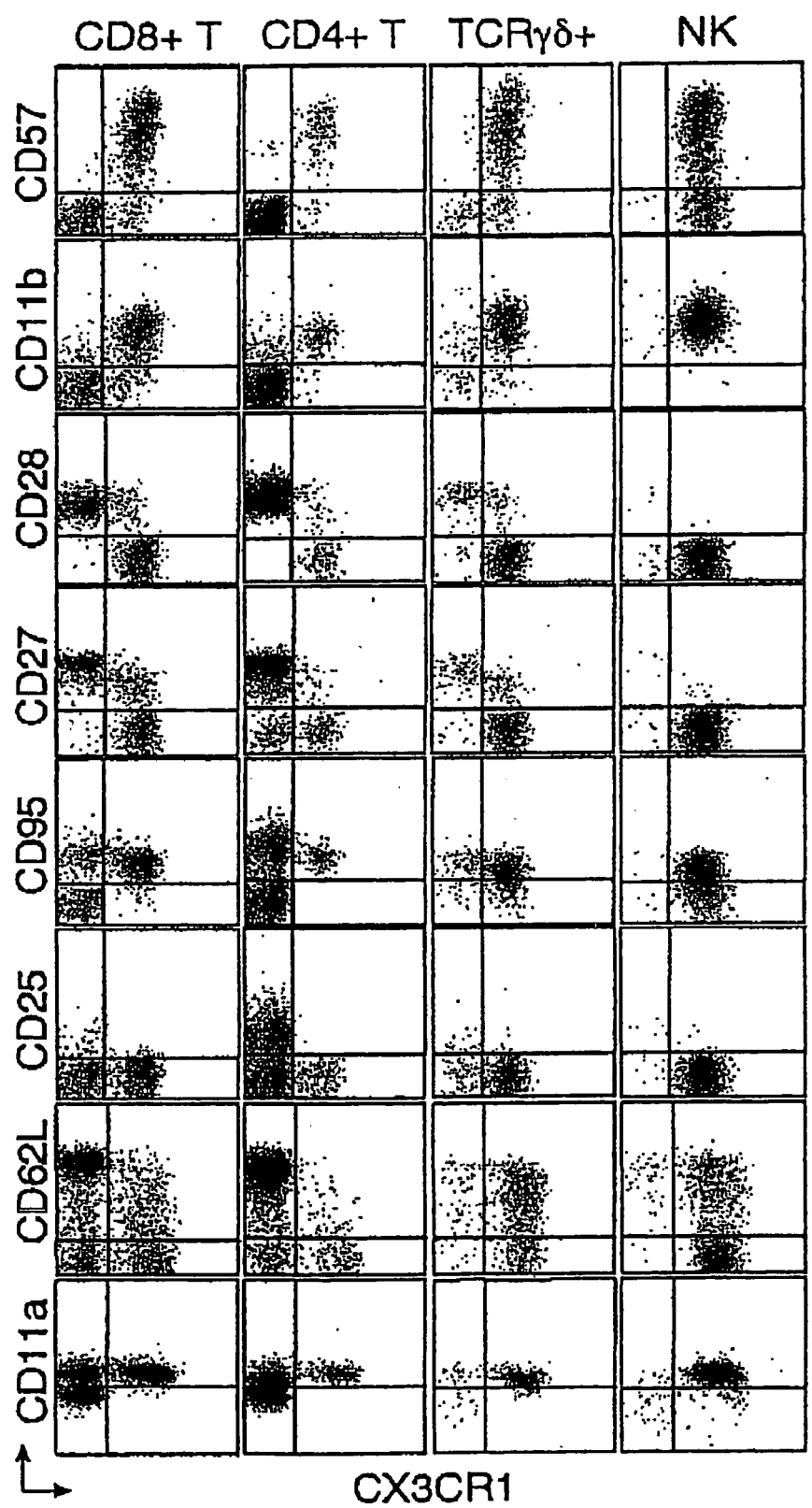
FIG. 2 shows correlations between CX3CR1-expressing cells and surface antigens of killer lymphocyte cells.

Since the expression subsets of CX3CR1-positive cells and abundance ratio thereof in lymphocytes correlated well with the expression subsets of killer lymphocytes and abundance ratios thereof in NK cells, CD8$^+$ T cells, CD4$^+$ T cells and TCR $\gamma\delta^+$ T cells, the relationship between the functional and activated cell surface markers and CX3CR1 expression was then examined (FIG. 2). As a result, in any subset including the NK cells, CD8$^+$ T cells, CD4$^+$ T cells and TCR $\gamma\delta^+$ T cells, the majority of CX3CR1-expressing cells were positive for CD57 and CD11b, which are killer cell surface markers, negative for CD27 and CD28, which are auxiliary stimulating molecules, slightly positive for Fas (CD95), which is an apoptosis stimulus-inducing receptor negative for CD25, which is an activation marker, negative or slightly positive for CD62L, which is a kind of selectin and strongly positive for CD11a, which is a kind of integrin.

These cell surface marker expression patterns were very similar to the reported expression patterns of CD8$^+$ effector killer T cells having cytotoxic activity. Further, since the similar patterns are also observed in NK cells having potent cytotoxic activity, it is inferred that the CX3CR1-expressing subsets of CD4$^+$ T cells and $\gamma\delta^+$ T cells also have cytotoxic activity. Therefore, it was considered that, although NK cells, CD8$^+$ T cells, CD4$^+$ T cells and TCR $\gamma\delta^+$ T cells had different cell activation mechanisms, CX3CR1 expression was characteristic of subsets having a common function, that is, effector killer lymphocytes having cytotoxic activity.

2) Correlation Between Expression of CX3CR1 and Expression of Perforin and Granzyme B Killer lymphocytes contain characteristic intracellular granules and stores perforin and granzyme B, which are cytotoxicity-inducing molecules, in these granules. These molecules are released from the granules towards target cells by an activation signal from T-cell receptors or NK-cell receptors and finally destroy the target cells. Then, to analyze whether or not CX3CR1 is selectively expressed in lymphocyte populations potentially having cytotoxic activity, correlation between expression of CX3CR1 and expression of intracellular perforin and granzyme B was analyzed.

Peripheral blood was collected from a vein of a healthy subject according to EDTA blood collection, and CX3CR1 and cell surface markers were stained as described above. Then, cells were suspended in 50 µL of the FACS solution, and 100 µL of IntraPrep Reagent 1 (Coulter) was added thereto. Then the mixture was left at room temperature for 15 minutes to fix the cells. The cells were washed once with PBS, suspended in 100 µL of IntraPrep Reagent 2 (Coulter) and left at room temperature for 5 minutes to induce permeability of cell membranes. Then, to the suspension, a PE-labeled anti-perforin antibody (PharMingen) or a PE-labeled anti-granzyme antibody (CLB or Caltag) was added, and the mixture was allowed to react at room temperature for 30 minutes. The cells were washed once with PBS, suspended in PBS containing 0.5% formalin and measured by using a FACS calibur (Becton-Dickinson).

Figure 3:
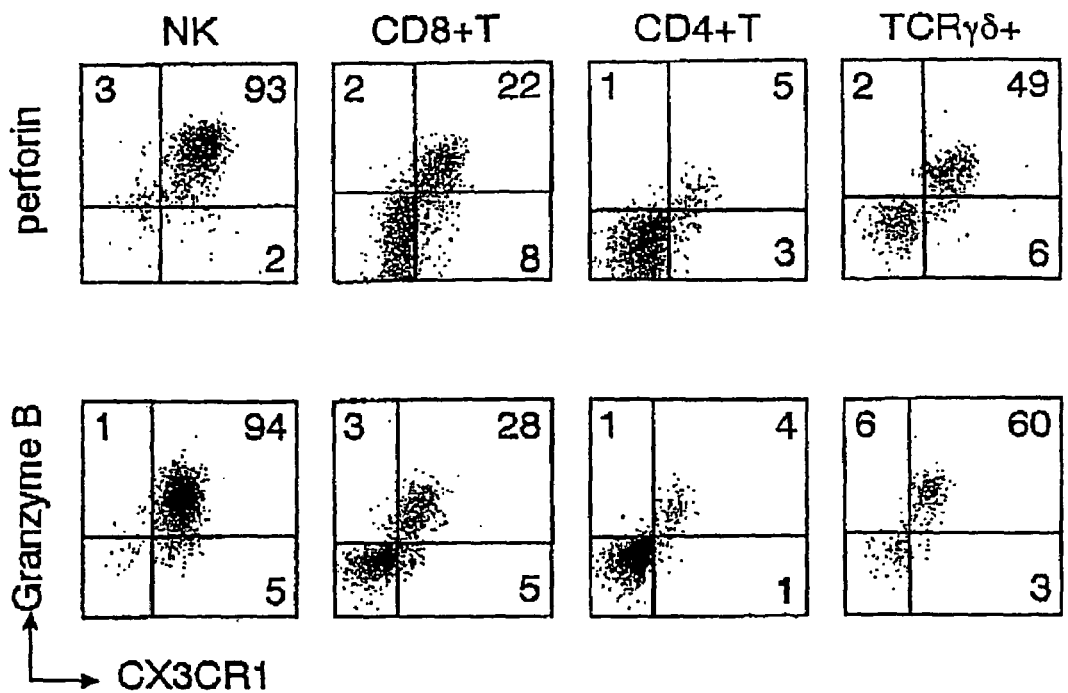
FIG. 3 shows correlations between expression of CX3CR1 and expressions of perforin and granzyme B.

As a result, among both of T cell subsets (CD4$^+$, CD8$^+$ or TCR $\gamma\delta^+$) and NK cells, cells potently expressing perforin and cells expressing granzyme B were locally observed in CX3CR1-expressing cells (FIG. 3). Therefore, it was further strongly demonstrated that CX3CR1 was selectively expressed in a majority of peripheral blood killer lymphocytes.

Example 3

Correlation Between Expression of CX3CR1 and Killer Activity

The correlation between expression of CX3CR1 and cytotoxic activity was analyzed. Since it was evident that a majority of NK cells expressed CX3CR1 and had cytotoxic activity, T cells were analyzed. Since, among T cells, a small number of CD4$^+$ T cells and TCR $\gamma\delta^+$ T cells were CX3CR1-positive cells and hence it was difficult to perform experiments using them, CD8$^+$ T cells were used as a representative to perform experiments. The CD8$^+$ T cells were purified twice by positive selections using MACS.

First, peripheral blood was collected from a vein of a healthy subject according to EDTA blood collection, and diluted two-fold with 1 mM EDTA/PBS. 3 ml of Ficol-Paque was introduced into a 15-ml centrifugation tube and overlaid with 10 ml of the diluted peripheral blood. The mixture was centrifuged at 1,550 rpm at room temperature for 25 minutes to separate mononuclear cell fraction, and the mononuclear cells were collected and washed twice with 1 mM EDTA/PBS. The mononuclear cells were washed once with PBS, and then 4×10$^7$ of the cells were suspended in 70 µL of a MACS solution (PBS containing 1% fetal calf serum (FCS) and 5 mM EDTA). To the mixture, 20 µl of FcR-blocking solution (Milteny) was added to block the Fc receptor.

Subsequently, 10 µL of CD8 microbeads (Milteny) were added and mixed by inversion at 4° C. for 20 minutes. The cells were washed with the MACS solution, suspended in 400 µL of the MACS solution per $10^7$ mononuclear cells and applied to an LS column (Milteny) attached to a Midi MACS magnet (Milteny). The column washed with the MACS solution and removed from the magnet, and a $CD8^+$ fraction was eluted with the MACS solution. Further, the $CD8^+$ fraction was added to a new LS column and the same operation was performed to obtain twice-purified $CD8^+$ fraction. When the cells obtained were analyzed by FACS, 97% or more of $CD8^+$ T cells were $CD3^+$ $CD8^+$ $CD16^-$ $CD8^+$ T cells.

Then, the $CD8^+$ T cells were separated and purified into CX3CR1-positive and CX3CR1-negative fractions by using a cell sorter. First, the purified $CD8^+$ T cells were suspended in the FACS solution, and an anti-human CX3CR1 monoclonal antibody was added. Then the mixture was allowed to react on ice for 30 minutes. The cells were washed twice with a staining solution, and a FITC-conjugated anti-rat IgG (H+L) antibody (Cedarlane) was added. Then the mixture was allowed to react on ice for 30 minutes. The cells were washed twice with a staining solution and CX3CR1-positive and CX3CR1-negative fractions were separately obtained by using a FACS Vantage (Becton-Dickinson). Each had a purity of 95% or higher. The cytotoxic T cell (CTL) activities of $CD8^+$ T cells (before separation into CX3CR1-positive and CX3CR1-negative cells), CX3CR1-positive $CD8^+$ T cells and CX3CR1-negative $CD8^+$ T cells were measured.

The CTL activity was measured by a CD3-antibody-dependent europium release experiment. $2\times10^6$ of mastcytoma P815 expressing the Fc receptor were suspended in 1 mL of a labeling solution (mixed solution of 880 µl of HEPES solution (50 mM HEPES, 93 mM NaCl, 5 mM KCl, 2 mM $MgCl_2$, pH 7.4), 140 µl of dextran sulfate stock solution (HEPES solution containing 0.5% dextran sulfate (MW 500,000)) and 80 µl of europium stock solution (mixed solution of 1.52 ml of europium atomic absorption standard solution (Aldrich), 0.5 ml of 100 mM diethylenetriaminepentaacetic acid (DTPA) solution and 7.98 ml HEPES solution)) and left at 37° C. for 20 minutes. The labeled cells were washed twice with a repairing solution (HEPES solution containing 2 mM $CaCl_2$, and 10 mM glucose) and then three times with RPMI-1640/ 10% FCS.

Subsequently, 5000 labeled cells were mixed so as to obtain various ratios of target cells and effector cells (ET ratio) and cultured in the presence of a CD3 antibody (clone UCHT-1, Genzyme). The experiment was performed in triplicate per one measurement point. The cells were cultured at 37° C. for 3 hours, and 60 µl of culture supernatant was recovered. Then 140 µl of enhancement solution (Wallac-Berthold) was added thereto and it was stirred at room temperature for 5 minutes. The time-resolved fluorescence was measured by using an ARVO-1240sx (Wallac-Berthold). The specific cytotoxic activity was calculated in accordance with the following equation: Percentage of specific target cell disruption=100×[(Europium release by experiment–Spontaneous europium release)/(Maximum europium release–Spontaneous europium release)]

Figure 4:
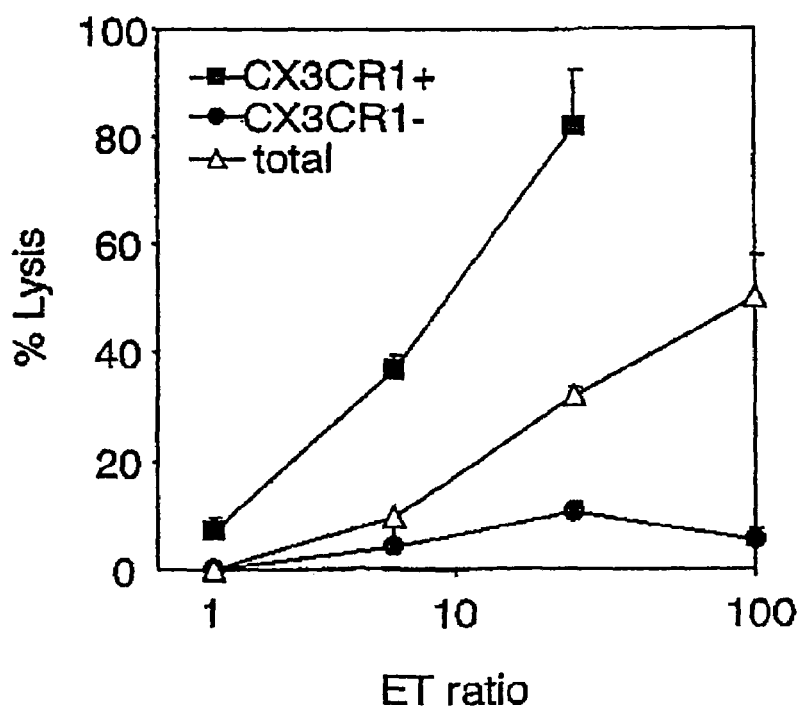
FIG. 4 shows correlations between expression of CX3CR1 and killer activity.

As a result, it was found that CX3CR1-positive $CD8^+$ T cells showed high cytotoxic activity, and the activity was obviously stronger than that of the $CD8^+$ T cells before the separation (FIG. 4). The CX3CR1-negative $CD8^+$ T cells rarely showed activity for disrupting target cells. It had been confirmed that these cytotoxic activities were CD3 dependent and that the binding of the anti-CX3CR1 antibody to cells used for cell sorting did not affect the cytotoxic activity. Therefore, it was revealed that CX3CR1 was selectively expressed in cytotoxic lymph-cells.

Example 4

Expression of CX3CR1 and Chemotaxis Activity of Killer Lymphocytes

The selective expression of CX3CR1 in cytotoxic lymph-cells strongly suggests that CX3CR1 is involved in chemot-axis of these cells. Therefore, lymphocyte subsets that migrated in response to fractalkine, which is a ligand of CX3CR1, was analyzed. The chemotaxis activity was measured by using the activity of peripheral blood mononuclear cells to transmigrate through ECV304 cells as an index.

$2\times10^5$ of ECV304 cells were introduced into a trans-well culture insert having a pore size of 5 µm (Coaster) and cultured in a M199/10% FCS culture broth for a few days to form a monolayer of ECV304 cells on the upper surface of the culture insert. Fractalkine was diluted with a chemotaxis solution (RPMI-1640:M199=1:1, 0.5% BSA, 20 mM HEPES, pH 7.4) to a concentration of 10 nM and added to a 24-well plate in an amount of 60011 per well. The trans-well culture insert, on which the ECV304 cells were cultured, was mounted on a 24-well trans-well and 106 peripheral blood mononuclear cells were suspended in 100 µl of the chemotaxis solution was added thereto. The cells were cultured at 37° C. for 4 hours, and cells that transmigrated through the ECV304 cells to the well plate were recovered, fluorescence-stained by using cell surface markers or intracellular antigens and quantified by using a FACS calibur.

Figure 5:
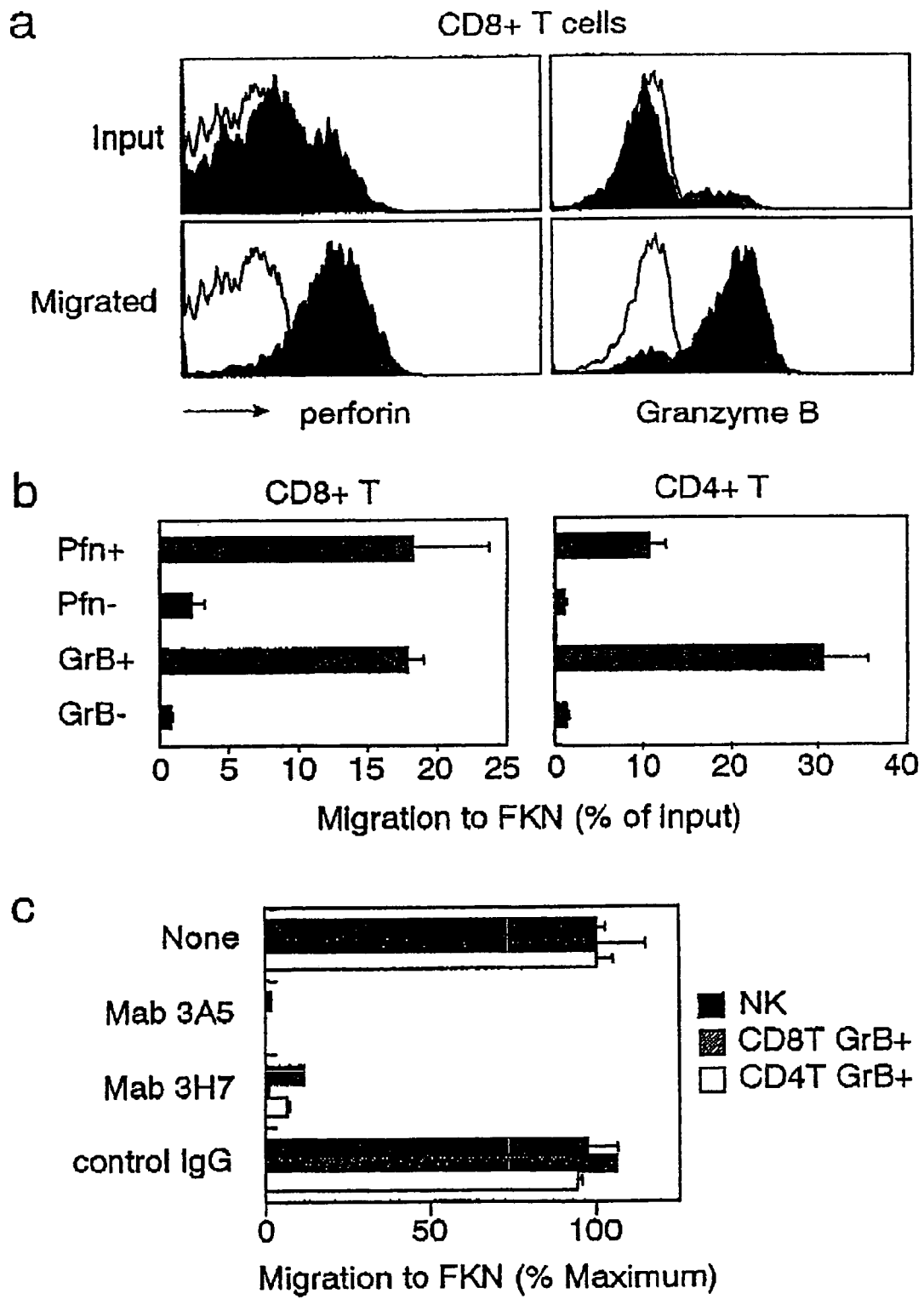
FIG. 5 shows CX3CR1 expression and killer lymphocyte chemotaxis activity.

As a result, it was found that, for both of $CD8^+$ T cells and $CD4^+$ T cells, the cell populations that migrated in response to fractalkine showed markedly increased ratios of perforin-positive cells and granzyme-B-positive cells compared with those of the populations before chemotaxis (FIG. 5, a). When the chemotaxis efficiency was calculated for each subset, it was revealed that fractalkine specifically induced cell chemo-taxis of perforin-positive cells and granzyme-B-positive cells for both of $CD8^+$ T cells and $CD4^+$ T cells (FIG. 5, b).

Further, cell chemotaxis of NK cells, granzyme-B-positive $CD8^+$ T cells and granzyme-B-positive $CD4^+$ T cells induced by fractalkine was suppressed by neutralizing antibodies against fractalkine (3A5-2 and 3H7-6) (FIG. 5, c). The neutralizing antibodies were diluted with the chemotaxis solution to a final antibody concentration of 50 µl/ml and added to the ECV304 cell layer 10 minutes before the start of the chemo-taxis reaction.

Therefore, it was revealed that the cell chemotaxis of killer lymphocytes could be suppressed by inhibiting the fractalk-ine-CX3CR1 interaction.

The neutralizing antibody against fractalkine was prepared as follows. As an antigen, human fractalkine was expressed in insect cells by using baculovirus as a fusion protein in which His tag was added to the C-terminus, and purified from the culture supernatant by using a chelate column (Imai, T et al., Cell, 91: 521-530, 1997). The antigen was mixed with Titer-Max adjuvant, and BALB/c mice were immunized with the mixture and thereafter immunized only with the antigen as booster. The antibody titer in the serum was measured by ELISA. Lymphocytes were isolated from a mouse having an increased antibody titer, and mixed with P3 myeloma cells at a ratio of lymphocytes:P3 myeloma cells=5:1 and cell fusion was attained by using PEG (Boehringer). Hybridomas were cultured in a 96-well plate for 1 week by using RPMI-1640/ 10% FCS/HAT/10% Origen HCF (ISGN). Then, ELISA was performed by using the culture supernatant to identify positive wells. The hybridomas producing an anti-human fracta-lkine antibody were cloned by two limiting dilutions. The monoclonal antibody was purified by using a protein A column from ascites prepared by inoculating the hybridoma into a BALB/c mouse to which incomplete Freund's adjuvant was administered. The neutralizing activity was measured by using suppression of chemotaxis of CX3CR1-expressing cells in response to human fractalkine as an index, and thus the neutralizing antibodies were obtained (3A5-2 and 3H7-6).

Example 5

Correlation Between Expression of Chemokine Receptors other than CX3CR1 and Killer Lymphocyte Whether or not expression of CX3CR1 specific for killer lymphocytes is characteristic of CX3CR1 that is not observed in other chemokine receptors was analyzed.

Figure 6:
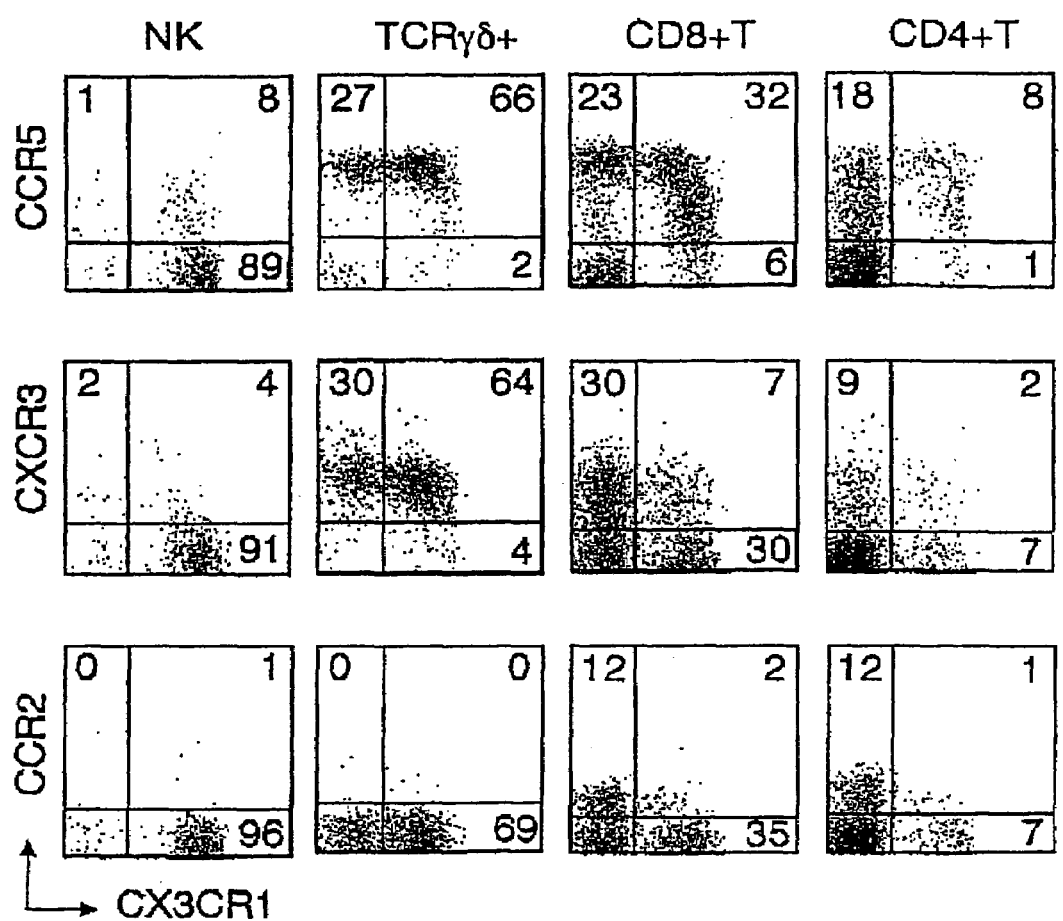
FIG. 6 shows correlations between expressions of chemokine receptors other than CX3CR1 and expression of CX3CR1.

Peripheral blood was double-stained with antibodies directed to CX3CR1 and other chemokine receptors to examine the correlation between expression of CX3CR1 and expression of other chemokine receptors (FIG. 6).

As a result, it was found that expression of CX3CR1 was observed in a majority of NK cells, but expression of CCR2, CCR5 and CXCR3 was not observed in the majority. Expression of CX3CR1 was observed in a part of TCR $\gamma\delta^+$ T cells, but CCR5 and CXCR3 were expressed in the majority. Among $CD8^+$ T cells and $CD4^+$ T cells, expression of CX3CR1 was observed in a part of CCR5-positive cells and expression of CX3CR1 was observed only in a small part of CCR5-negative cells. CCR2 and CXCR3 were not expressed in a majority of CX3CR1-positive cells. Therefore, it was revealed that expression of CX3CR1 had a characteristic different from those of other chemokine receptors and only expression of CX3CR1 was specific for killer lymphocytes.

Example 6

Effect of Membrane-Bound Fractalkine on Chemotaxis in Response to MIP-1α, MIP-1β and MCP-1

It is known that cell adhesion of membrane-bound fractalkine and CX3CR1 induces capture, firm adhesion and activation of lymphocytes. Therefore, effect of fractalkine expressed on the cell membrane on chemotaxis in response to MIP-1α, MIP-1β and MCP-1 was examined. ECV304 cells and fractalkine-expressed ECV304 cells (Imai, T et al., Cell, 91: 521-530, 1997) were used in the experiment and effect on chemotaxis of peripheral blood mononuclear cells was observed by the same method as in Example 4.

Figure 7:
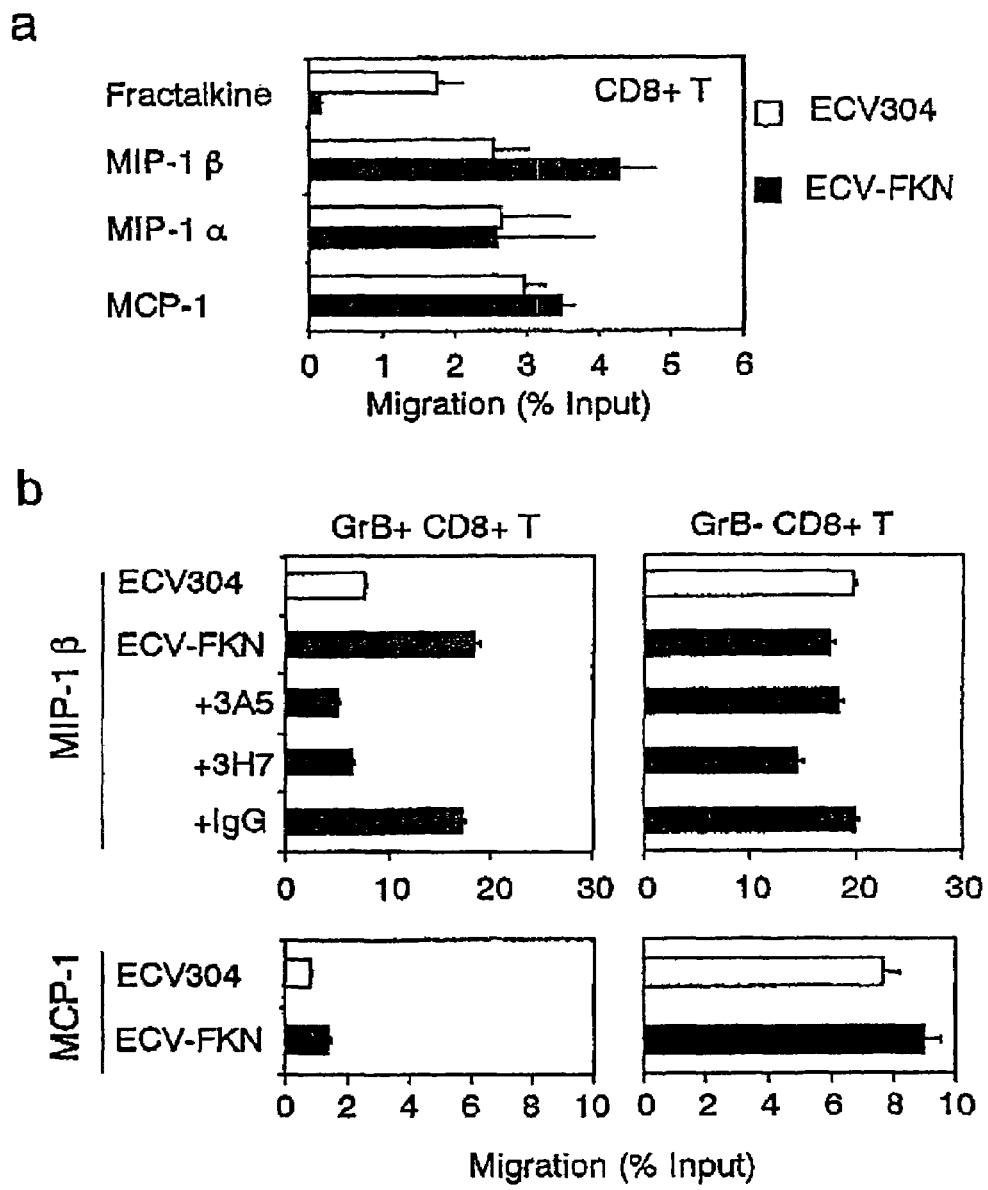
FIG. 7 shows effect of membrane-bound fractalkine on chemotaxis of killer lymphocytes in response to MIP-1α, MIP-1β and MCP-1.

As a result, when the membrane-bound fractalkine (fractalkine-expressing ECV304 cells) was used, chemotaxis of $CD8^+$ T cells in response to MIP-1β was enhanced, whereas effect on chemotaxis in response to MIP-1α and MCP-1 was not observed (FIG. 7, 1).

Therefore, $CD8^+$ T cells were classified into granzyme-B-positive cells and granzyme-B-negative cells to perform a chemotaxis experiment (FIG. 7, b). With respect to MIP-1β, when ECV304 cells were used, chemotaxis of granzyme-B-negative cells was preferentially induced. However, when membrane-bound fractalkine was used, only chemotaxis of granzyme-B-positive cells was strongly enhanced and enhancement of chemotaxis of granzyme-B-negative cells was hardly observed. On the other hand, with respect to MCP-1, when either ECV304 cells or fractalkine-expressing ECV304 cells were used, chemotaxis of granzyme-B-negative cells was specifically induced and almost no chemotaxis of granzyme-B-positive cells was observed. Further, enhancement of chemotaxis by membrane-bound fractalkine was not observed in the case of MCP-1.

Further, with respect to MIP-1α, it was observed only that chemotaxis of granzyme-B-positive cells in a part of donors tended to be selectively and slightly enhanced by membrane-bound fractalkine.

Further, enhancement effect on chemotaxis of granzyme-B-positive cells in response to MIP-1β by membrane-bound fractalkine was suppressed by treatment with the neutralizing antibodies against fractalkine (3A5-2 and 3H7-6). The neutralizing antibodies were diluted with the chemotaxis solution to an antibody concentration of 50 μl/ml and added to the ECV304 cell layer 10 minutes before the start of a chemotaxis reaction.

From the above results, it was revealed that membrane-bound fractalkine specifically enhanced cell chemotaxis of CX3CR1-expressing killer lymphocytes as for chemotaxis in response to MIP-1β. Further, this cell chemotaxis enhancing action was observed when MIP-1β, whose receptor was CCR5 coexpressed with CX3CR1 at a high probability, was used as a chemotactic factor, but was not observed in response to MCP-1, whose receptor was CCR2 hardly coexpressed with CX3CR1.

Therefore, it was suggested that fractalkine on the ECV304 cell membrane enhanced cell chemotaxis induced by other chemokines, through adhesion or activation mediated by CX3CR1. Further, it was revealed that cell chemotaxis of killer lymphocytes induced by another chemokine, MIP-1β, could be suppressed by inhibiting an interaction between fractalkine and CX3CR1.

Example 7

Effect of Anti-Fractalkine Antibody in ConA-Induced Hepatitis Model

ConA-induced hepatitis is considered an autoimmune hepatopathy model, and involvement in it, of lymphocytes having cytotoxic activity such as NK cells and NKT cells has been reported. Therefore, effect of an anti-fractalkine antibody on this model was examined.

The anti-fractalkine antibody was prepared as follows. As an antigen, mouse fractalkine produced by R&D was used. The antigen was mixed with TiterMax adjuvant, and Armenian hamsters were immunized with the mixture and thereafter additionally immunized only with the antigen as booster. The antibody titer in serum was measured by ELISA. Lymphocytes were isolated from an Armenian hamster having an increased antibody titer, and mixed with P3 myeloma cells at a ratio of lymphocytes:P3 myeloma cells=5:1, and cell fusion was attained by using PEG (Boehringer). Hybridomas were cultured on a 96-well plate for 1 week by using RPMI-1640/10% FCS/HAT/10% Origen HCF (ISGN). Then, ELISA was performed by using each culture supernatant to identify positive wells. A hybridoma producing an anti-mouse fractalkine antibody was cloned by two limiting dilutions. The monoclonal antibody was purified by using a protein A column from ascites prepared by inoculaging the hybridoma into a SCID mouse to which incomplete Freund's adjuvant was administered. The neutralizing activity was measured by using suppression of chemotaxis of CX3CR1-expressing cells in response to mouse fractalkine as an index to obtain a neutralizing antibody (5H8-4).

To each group of five C57B/6 mice, PBS (phosphate buffer), 500 μg of control antibody (hamster IgG), 250 μg or 500 μg of anti-fractalkine antibody (5H8-4) (antibody dissolved in PBS solution) was intravenously administered and immediately thereafter 12 mg/kg concanavalin A (ConA) was intravenously administered. After 12 hours, blood was collected from abdominal portion of vena cava in the presence of heparin, and ALP, GOT and GPT in plasma were measured by using Olympus AU600.

Further, to each group of four C57B/6 mice, PBS, a control antibody or 500 μg of anti-fractalkine antibody and then ConA was administered as described above. Concentrations of TNF and IFNγ in plasma after 2 hours were measured by using an ELISA kit (Biosource).

Figure 8:
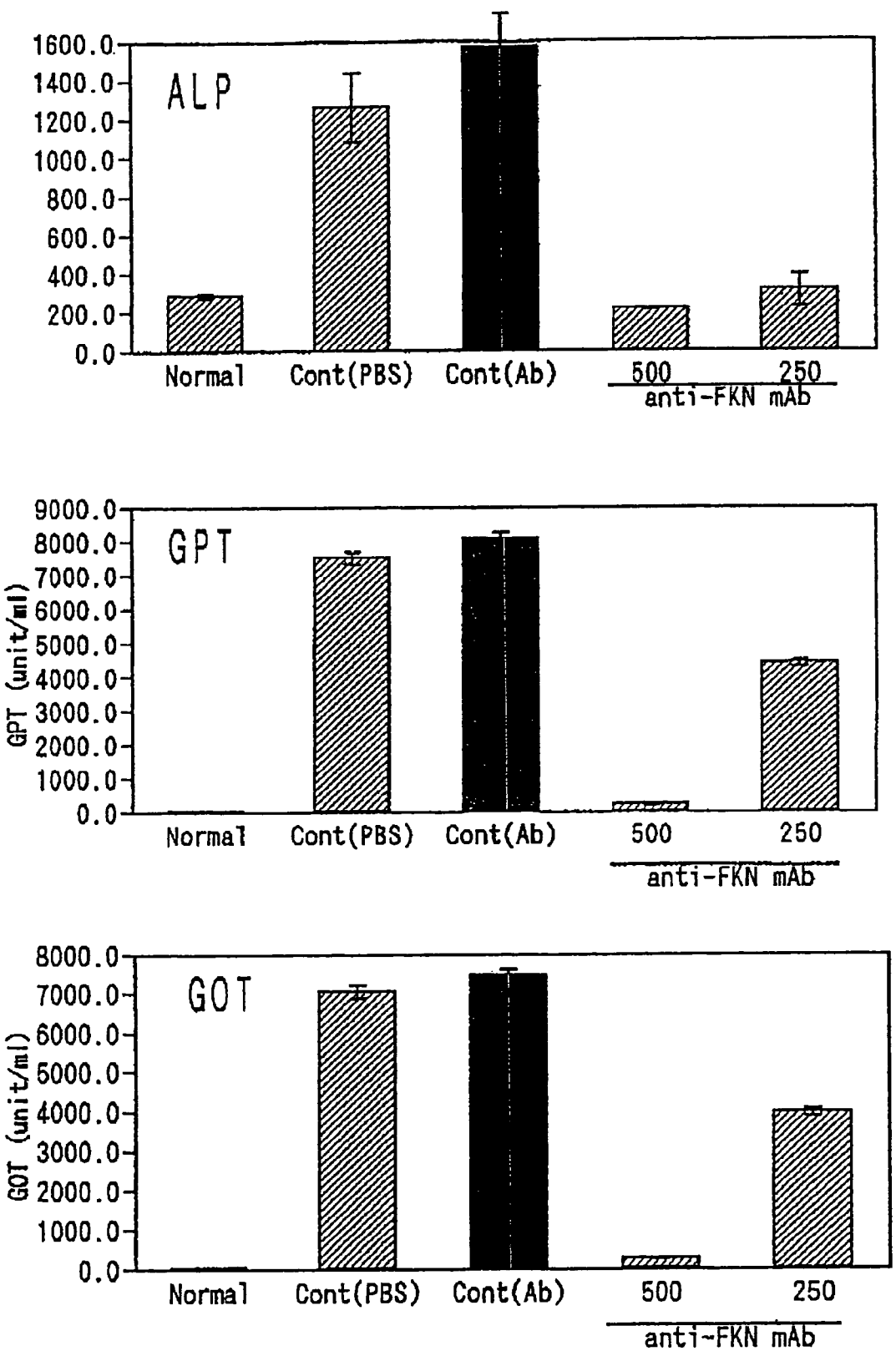
FIG. 8 shows effect of an anti-fractalkine (FKN) monoclonal antibody on ConA-induced hepatitis in a mouse.
Figure 9:
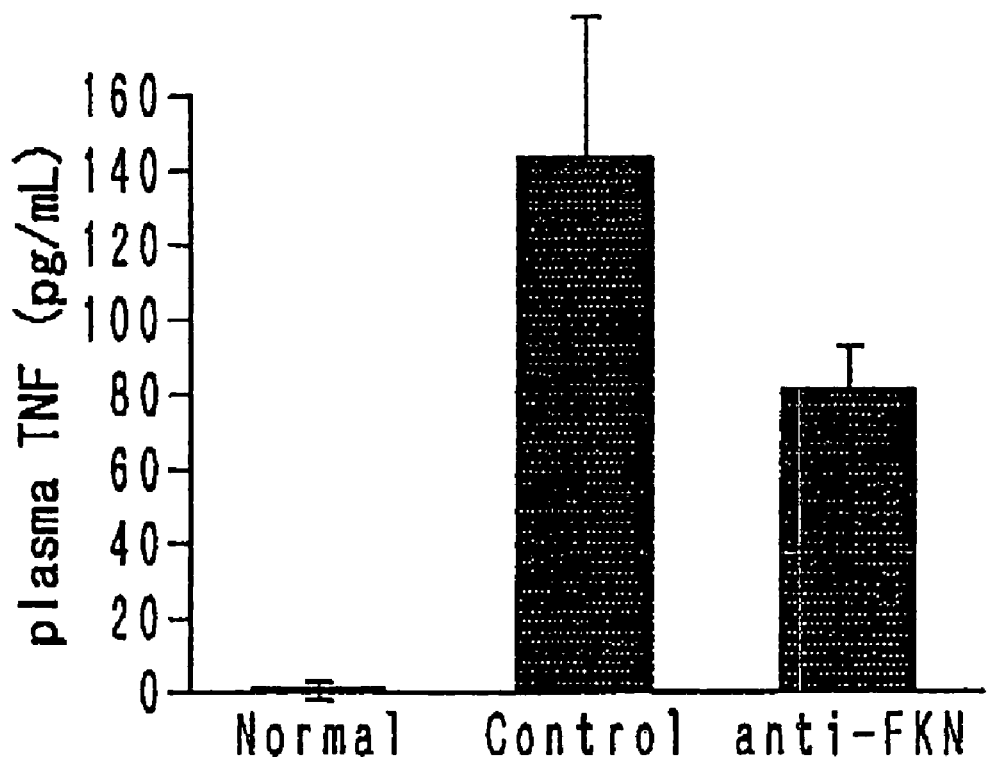
FIG. 9 shows effect of an anti-fractalkine (FKN) antibody on increase of cytokines 2 hours after injection of ConA.
Figure 9:
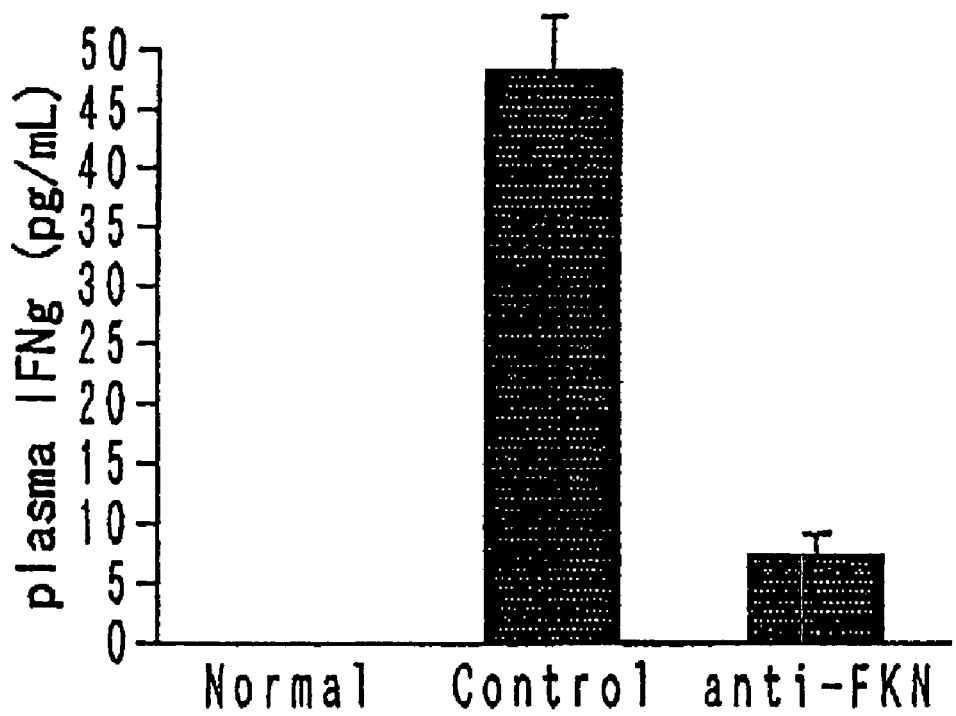

The results are shown in FIGS. 8 and 9. As shown in FIGS. 8 and 9, ALP, GOT and GPT elevated by administration of ConA were decreased by administration of the anti-fractalkine antibody and the concentrations of TNF and IFNγ in blood were also decreased at the same time.

From the above results, it was found that the fractalkine-CX3CR1 pathway played an important role in ConA-induced hepatitis. Further, an action for suppressing production of cytokines such as TNF and IFNγ was suggested as the suppression mechanism therefor. It was suggested that suppression of the fractalkine-CX3CR1 pathway would be useful for treatment of autoimmune hepatitis (autoimmune disease).

Example 8

Effect of Anti-Fractalkine Antibody on Experimental Autoimmune Encephalomyelitis (EAE)

EAE is a demyelinating encephalomyelitis induced by immunization with a myelin-constituting protein and regarded as a model of multiple sclerosis (MS). Its symptoms include quadriplegia, and infiltration of lymphocytes is observed in lesions. CX3CR1 is expressed on a glia cell, and it is considered that a stimulus from fractalkine plays an important role in production of chemokines such as MCP-1 and MIP-1. Therefore, effect of the anti-fractalkine antibody on the EAE model was examined.

Each C57B/6 mouse of a group consisting of four mice was immunized with 100 μg of MOG peptide (myeline oligodendrocyte glycoprotein, a peptide having a sequence of MEVG-WYRSPFSRVVHLYRNGK (SEQ ID NO: 1), synthesis was entrusted to Toray Research Center) together with adjuvant, and 30 ng of pertussis toxin was intravenously administered on the day of immunization and 2 days later. To each of the mice, 500 μg of the anti-fractalkine antibody (5H8-4) was intraperitoneally administered twice a week from day 5 after the immunization. The mice were evaluated with the following scores.

0: No onset, 1: chalasia of tail, 2: slight palsy of fore-limb or loss of righting reflex, 3: complete palsy of hind-limb; 4: palsy of fore-limb or low of righting reflex; 5: death.

Figure 10:
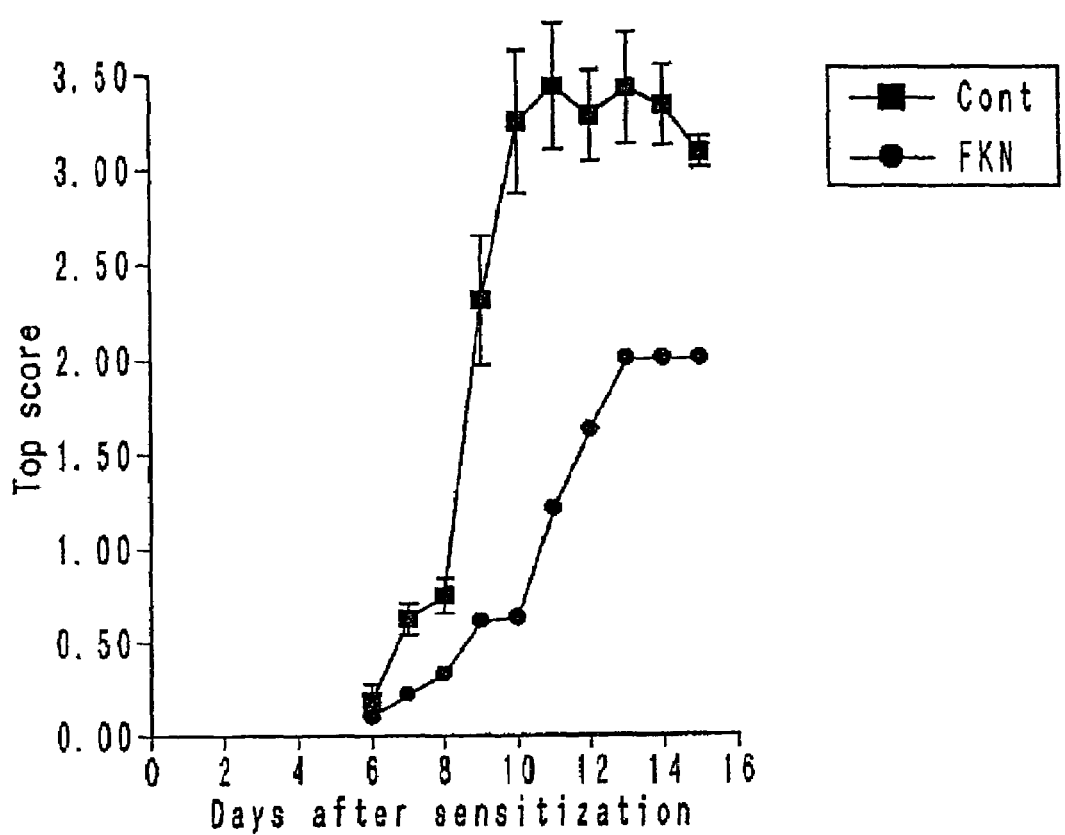
FIG. 10 shows effect of an anti-fractalkine (FKN) antibody on experimental autoimmune encephalomyelitis.

The results are shown in FIG. 10. As shown in FIG. 10, the anti-fractalkine antibody alleviated symptoms in the EAE model, and thus it was suggested that blocking of the fractalkine-CX3CR1 pathway was useful for treatment of multiple sclerosis.

Example 9

Cytotoxicity of Saporin-Labeled Anti-CX3CR1 Antibody to CX3CR1-Expression Cells

As a model system selectively damaging CX3CR1-expressing killer cells, cytotoxicity of a saporin-labeled 2A9-1 antibody to cells to which the CX3CR1 gene was introduced to express CX3CR1 was examined.

1. Preparation of Mouse Cell Expressing Fusion Protein of Human CX3CR1 Receptor and EGFP By using human CX3CR1 cDNA (Imai, T et al., Cell, 91: 521-530 (1997)), a gene fragment in which a termination codon was eliminated from the full length of the protein coding region was amplified by PCR. The obtained gene fragment was digested with restriction enzymes SalI and XbaI and inserted into an SalI/XbaI site of EGFP fusion protein expression vector pEGFP-N1 (Clontech) upstream from EGFP to prepare a gene fragment coding for a CX3CR1-EGFP fusion protein. The prepared gene fragment was digested with SalI and NotI to excise a fragment, and it was inserted into an SalI/NotI site of a mammalian cell retrovirus expression vector (pMX) to construct a mammalian cell expression vector (pMX V28-EGFP). This vector was introduced into a packaging cell (BOSC23) by the lipofection method, and a recombinant retrovirus was produced in a culture supernatant. This recombinant retrovirus was infected into a mouse pre-B cell strain (L1.2) in the presence of polybrene. The CX3CR1-EGFP-expressing cells were fractionated and collected by a FACS Caliber (Becton Dickinson). As a result, the L1.2 cell population, in which about 90% of cells expressed CX3CR1-EGFP, was obtained.

Figure 11:
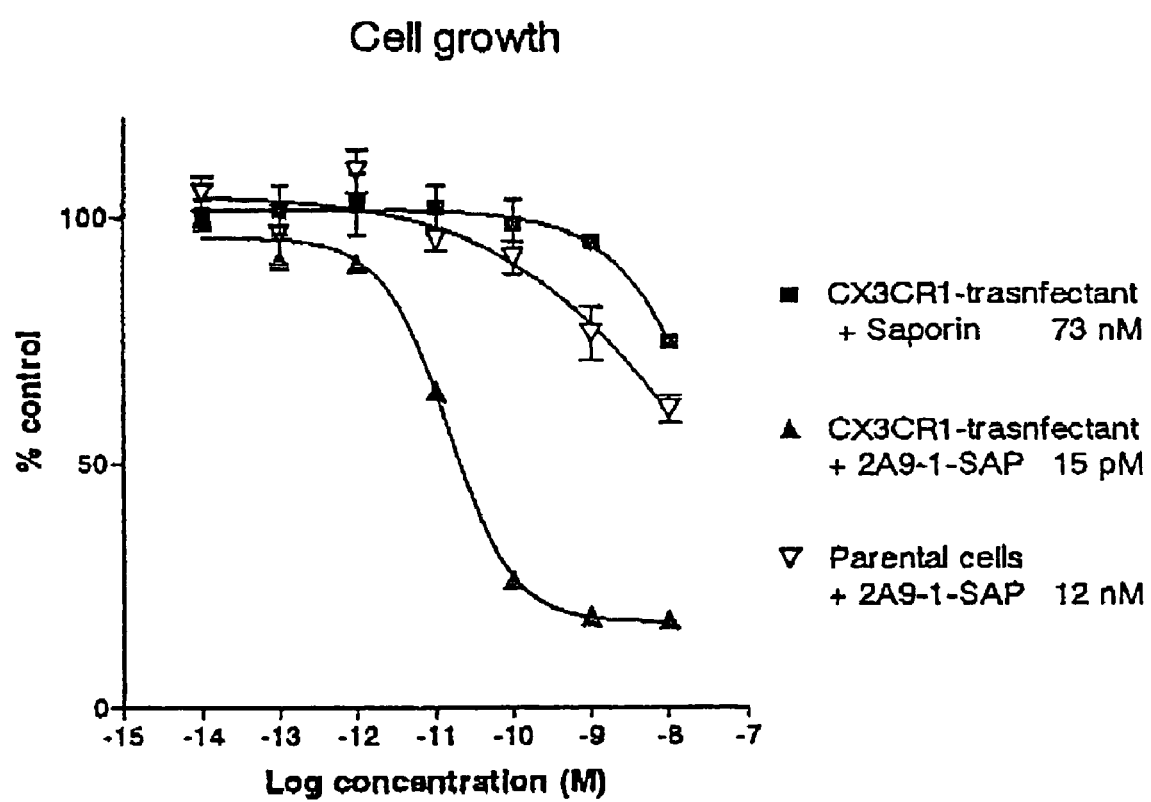
FIG. 11 shows cytotoxicity of a saporin-labeled anti-CX3CR1 antibody on CX3CR1-expressing cells.

2. CX3CR1-Expressing Cell-Specific Growth Suppression by Saporin-Labeled Anti-CX3CR1 Antibody The saporin labeling of 2A9-1 antibody was entrusted to Advanced Targeting Systems to obtain a saporin-labeled 2A9-1 antibody. Further, saporin as a control was purchased from Advanced Targeting Systems. An amount of $10^3$ per well of L1.2 parent strain or CX3CR1-EGFP-expressing L1.2 cells were introduced into each well of a 96-well plate, and a saporin or saporin-labeled 2A9-1 antibody diluted to a concentration of $10^{-8}$ to $10^{-14}$ was added thereto. Then they were cultured in a $CO_2$ incubator for 2 days by using 200 μl of RPMI-1640/10% FCS culture broth. Then, the cells were suspended, and the LDH activity contained in 20 μl of cell suspension was measured and used as an index for number of living cells. As a result, it was found that the saporin-labeled 2A9-1 antibody showed CX3CR1-expressing cell-specific growth suppression (FIG. 11). The $IC_{50}$ values calculated by Graphpad Prism software program were 15 pM for the saporin-labeled 2A9-1 antibody with respect to the CX3CR1-expressing cells, 12 nM for the saporin-labeled 2A9-1 antibody with respect to the parent strain L1.2 cells and 73 nM for saporin with respect to the CX3CR1-expressing cells. Therefore, it was revealed that the saporin-labeled 2A9-1 antibody had 1000 times or more higher specificity for the CX3CR1-expressing cells. Therefore, it was demonstrated that an anti-CX3CR1 antibody labeled with a toxin such as saporin was effective as an immunotoxin.

What is claimed is:

1. A method for treating a subject in need thereof for an autoimmune disease, which comprises administering a therapeutically effective amount of a monoclonal antibody that binds to CX3CR1 or fractalkine and inhibits chemotaxis of killer lymphocytes by suppressing an interaction between CX3CR1 and fractalkine, wherein the autoimmune disease is autoimmune hepatitis, rheumatoid arthritis, or diabetes mellitus.

2. The method according to claim 1, wherein the autoimmune disease is autoimmune hepatitis.

3. The method for treating an autoimmune disease according to claim 2, wherein the antibody binds to fractalkine.

4. The method according to claim 1, wherein the autoimmune disease is rheumatoid arthritis.

5. The method for treating an autoimmune disease according to claim 4, wherein the antibody binds to fractalkine.

6. The method for treating an autoimmune disease according to claim 1, wherein the autoimmune disease is diabetes mellitus.

7. The method for treating an autoimmune disease according to claim 6, wherein the antibody binds to fractalkine.

* * * * *

SEQUENCE LISTING

<160> NUMBER OF SEQ ID NOS: 1

<210> SEQ ID NO 1
<211> LENGTH: 21

```
<212> TYPE: PRT
<213> ORGANISM: Artificial Sequence
<220> FEATURE:
<223> OTHER INFORMATION: synthetic peptide

<400> SEQUENCE: 1

Met Glu Val Gly Trp Tyr Arg Ser Pro Phe Ser Arg Val Val His Leu
 1               5                  10                  15

Tyr Arg Asn Gly Lys
            20
```